United States Patent
Desai et al.

(10) Patent No.: US 7,009,063 B2
(45) Date of Patent: *Mar. 7, 2006

(54) PROCESS FOR THE PRODUCTION OF OXANDROLONE

(75) Inventors: Shaileshkumar Ramanlal Desai, Wilmington, NC (US); David Wayne Ray, Jr., Wilmington, NC (US); Yousry A. Sayed, Wilmington, NC (US)

(73) Assignee: Barr Laboratories, Inc., Woodcliff Lake, NJ (US)

( * ) Notice: Subject to any disclaimer, the term of this patent is extended or adjusted under 35 U.S.C. 154(b) by 21 days.

This patent is subject to a terminal disclaimer.

(21) Appl. No.: 10/852,744

(22) Filed: May 24, 2004

(65) Prior Publication Data

US 2005/0004376 A1    Jan. 6, 2005

Related U.S. Application Data

(62) Division of application No. 10/014,665, filed on Dec. 11, 2001, now Pat. No. 6,787,659.

(51) Int. Cl.
*C07J 3/00* (2006.01)
*C07D 307/83* (2006.01)

(52) U.S. Cl. ...................................... 552/610; 549/243
(58) Field of Classification Search ................ 552/610; 549/243
See application file for complete search history.

(56) References Cited

U.S. PATENT DOCUMENTS

| | | | |
|---|---|---|---|
| 2,260,328 A | 10/1941 | Miescher et al. | |
| 2,305,602 A | 12/1942 | Butenandt et al. | |
| 2,879,279 A | 3/1959 | Burg | |
| 3,101,349 A | 8/1963 | Pappo et al. | |
| 3,109,016 A | 10/1963 | Nysted et al. | |
| 3,128,283 A | 4/1964 | Pappo et al. | |
| 3,246,014 A | 4/1966 | Jung et al. | |
| 3,280,133 A | 10/1966 | Pappo et al. | |
| 3,282,962 A | 11/1966 | Pappo et al. | |
| 3,644,342 A | 2/1972 | Chorvat et al. | |
| 3,666,775 A | 5/1972 | Uskokovic | |
| 3,673,217 A | 6/1972 | Uskokovic | |
| 3,761,503 A | 9/1973 | Uskokovic | |
| 3,761,504 A | 9/1973 | Uskokovic | |
| 3,843,685 A | 10/1974 | Uskokovic et al. | |
| 3,956,316 A | 5/1976 | Uskokovic et al. | |
| 4,097,678 A | 6/1978 | Kerb et al. | |
| 4,328,162 A | 5/1982 | Hyatt et al. | |
| 4,376,733 A | 3/1983 | Frimer | |
| 4,434,080 A | 2/1984 | Barton et al. | |
| 5,510,538 A | 4/1996 | Frigerio et al. | |
| 6,211,363 B1 | 4/2001 | Terasawa et al. | |
| 6,583,298 B1 | 6/2003 | Santa et al. | |
| 6,787,659 B1 * | 9/2004 | Desai et al. | ................ 552/610 |
| 2003/0032817 A1 | 2/2003 | Cabaj et al. | |
| 2003/0109721 A1 | 6/2003 | Desai et al. | |

FOREIGN PATENT DOCUMENTS

| | | |
|---|---|---|
| WO | WO 98/24452 | 6/1998 |
| WO | 0114348 | 3/2001 |
| WO | WO 02/100881 | 12/2002 |

OTHER PUBLICATIONS

Bi, H., et al., "Studies on anabolic steroids. 9. Tertiary sulfates of anabolic 17 α-methyl steroids: synthesis and rearrangement", *Steroids, Structure, Function, and Regulation*, (Butterworth-Heinemann) 57(7): 306-312, 1992.

Carey, F. A., et al., "Part B: Reactions and Synthesis, Oxidations", *Advanced Organic Chemistry, Chapter 12*, (Plenum Press) 3: 625-626, 1990.

Counsell, R. E., et al., "Anabolic Agents. Derivatives of 5α-Androst-1-ene", *J. Organic Chem.*, (The Am. Chem. Soc.)27(1): 248-253, 1962.

Nicolaou, K. C., et al., "A New Method for the One-Step Synthesis of $\alpha,\beta$-Unsaturated Carbonyl Systems from Saturated Alcohols and Carbonyl Compounds", *J. Am. Chem. oc.*, (Am. Chem. Soc.)122: 7596-7597, 2000.

Pappo, R. and Jung, C. J., "2-Oxasteroids: A New Class of Biologically Active Compounds", *Tetrahedron Letters*, (Pergamon Press Ltd) 9: 365-371, 1962.

Pelc, B, "Steroid-Derivatives, XXIV.*, The Preparation of 17α-Methylandrost-1-EN-17β-OL-3-One", *Collection of Czechoslovak Chemical Communications*, (Czechoslovak Academy of Sciences) 29(4): 1029-1034, 1964.

Schänzer, W., et al., "17-Epimerization of 17 α-methyl anabolic steroids in humans: metabolism and synthesis of 17 α-hydroxy-17 β-methyl steroids", *Steroids*, (Butterworth-Heinemann) 57(11): 537-550, 1992.

* cited by examiner

Primary Examiner—Charanjit S. Aulakh
(74) Attorney, Agent, or Firm—Hutchison & Mason PLLC

(57) ABSTRACT

The present invention relates to a process for the synthesis of oxandrolone from mestanolone. The process comprises the steps of: (a) oxidizing mestanolone to form 17β-hydroxy-17α-methyl-5α-androst-1-en-3-one; (b) hydroxylating the 17β-hydroxy-17α-methyl-5α-androst-1-en-3-one to form 1α, 2α, 17β-trihydroxy-17α-methylandrostan-3-one; (c) cleaving the 1α, 2α, 17β-trihydroxy-17α-methylandrostan-3-one to form 17β-hydroxy-17α-methyl-1-oxo-1,2,-seco-A-nor-5α-androstan-2-oic acid; and (d) reducing the 17β-hydroxy-17α-methyl-1-oxo-1,2,-seco-A-nor-5α-androstan-2-oic acid to form oxandrolone.

11 Claims, 1 Drawing Sheet

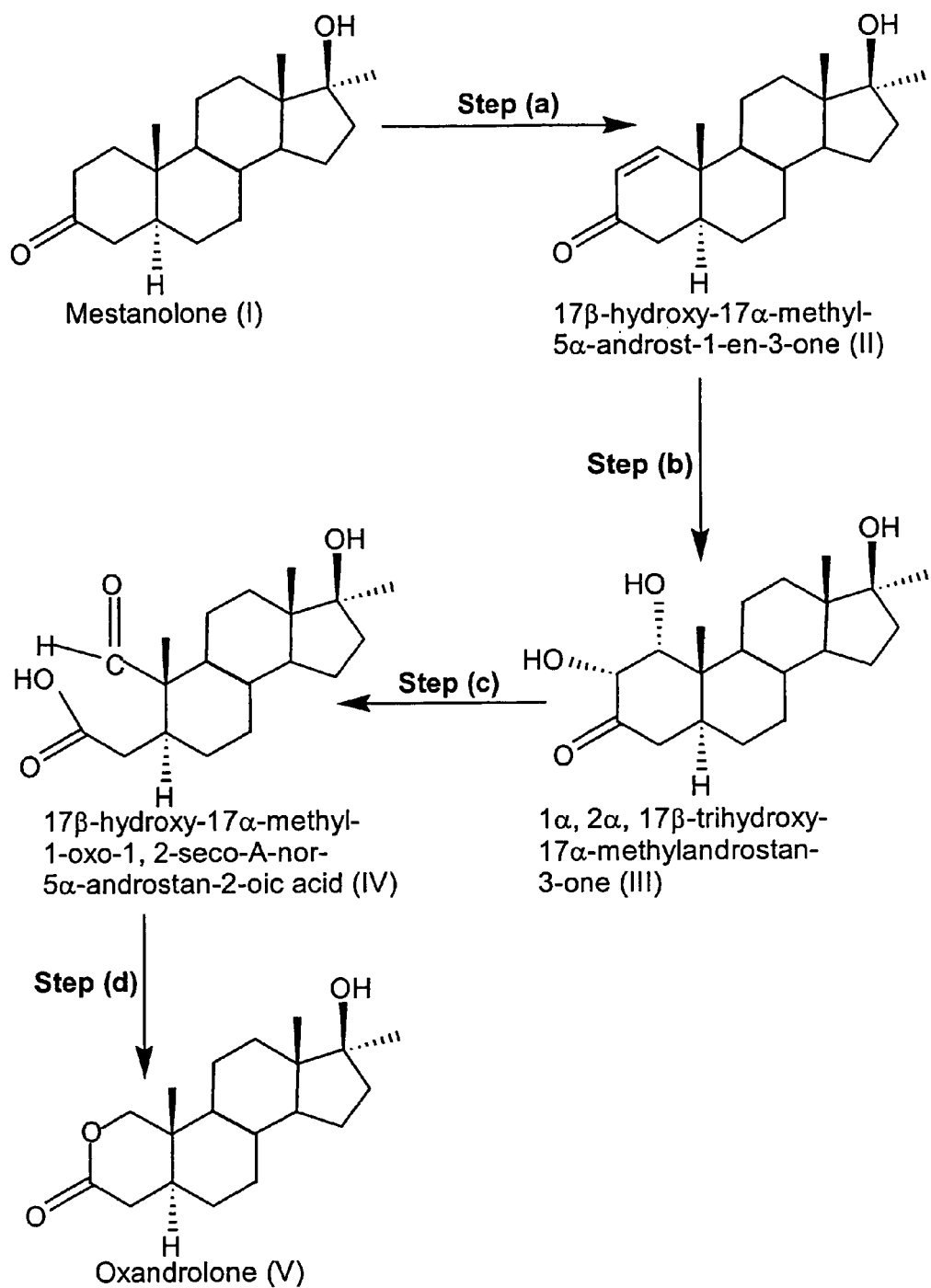
FIGURE

US 7,009,063 B2

PROCESS FOR THE PRODUCTION OF OXANDROLONE

RELATED APPLICATION

This application is a divisional of U.S. application Ser. No. 10/014,665, filed Dec. 11, 2001 now U.S. Pat. No. 6,787,659. The entire content of U.S. application Ser. No. 10/014,665 is hereby incorporated herein by reference.

FIELD OF THE INVENTION

The present invention relates to a process for the synthesis of oxandrolone. The present invention further relates to a process which provides oxandrolone in relatively high yields and purity.

BACKGROUND OF THE INVENTION

Oxandrolone (i.e., 17β-hydroxy-17α-methyl-2-oxa-5α-androstan-3-one) is a known anabolic steroid that has various therapeutic uses. Methods of producing oxandrolone are known. For example, U.S. Pat. No. 3,109,016 discloses a process of manufacture of 17-oxygenated 2-oxa-5α-androstan-3-ones. The '016 patent discloses the reaction of 17β-hydroxy-17α-methyl-5α-androst-1-en-3-one in methylene chloride and methanol with ozone to produce methyl 17β-hydroxy-17α-methyl-1-oxo-1,2,-seco-A-nor-5α-androstan-2-oate and, alternatively, with ozone in methylene chloride to yield 17β-hydroxy-17α-methyl-1-oxo-1,2,-seco-A-nor-5α-androstan-2-oic formic anhydride. According to the '016 patent, the 1,2-seco intermediates are converted to the corresponding anabolic 2-oxa compound by treatment with a reducing agent in aqueous medium. The methyl 17β-hydroxy-17α-methyl-1-oxo-1,2,-seco-A-nor-5α-androstan-2-oate may be contacted with sodium borohydride in aqueous sodium hydroxide to form 17β-hydroxy-17α-methyl-2-oxa-5α-androstan-3-one (i.e., oxandrolone).

U.S. Pat. No. 3,128,283, which relates to 17-oxygenated androstane and estrane derivatives in which the A ring contains a lactone structure, also discloses an example of the production of oxandrolone. 17β-hydroxy-17α-methyl-5α-androst-1-en-3-one is reacted in aqueous acetic acid with osmium tetroxide and lead tetracetate to afford 17β-hydroxy-17α-methyl-1-oxo-1,2,-seco-A-nor-5α-androstan-2-oic acid. This compound is converted to 17β-hydroxy-17α-methyl-2-oxa-5α-androstan-3-one by reduction with sodium borohydride in aqueous sodium hydroxide. A disadvantage of methods that use lead tetracetate, however, is that lead tetracetate is a highly toxic compound.

17-hydroxy-17-methyl-5-androst-1-en-3-one may be formed from 17-hydroxy-17-methyl-5-androstan-3-one. For example, U.S. Pat. No. 2,260,328 discloses mixing 17-hydroxy-17-methyl-5-androstan-3-one in glacial acetic acid solution with bromine. This product is precipitated and purified. The product is then heated with dimethylaniline or potassium acetate in glacial acetic acid under pressure to eliminate hydrogen bromide, thus forming 17-hydroxy-17-methyl-5-androst-1-en-3-one.

Methods using bromination-dehydrobromination are disadvantageous due to low yields. For example, these methods typically generate the compound in a 15-30% overall yield with the compound being contaminated in approximately 5–10% of methyl testosterone. Such methods generally require the use of chromatography such as silica gel chromatography to obtain pure product.

It would be advantageous to provide a process for producing oxandrolone that results in the formation of oxandrolone in relatively high yields and purity.

SUMMARY OF THE INVENTION

The present invention relates to a process for the synthesis of oxandrolone from mestanolone. In one aspect of the present invention, a process is provided comprising the steps of: (a) oxidizing mestanolone to form 17β-hydroxy-17α-methyl-5α-androst-1-en-3-one; (b) hydroxylating the 17β-hydroxy-17α-methyl-5α-androst-1-en-3-one to form 1α, 2α, 17β-trihydroxy-17α-methylandrostan-3-one; (c) cleaving the 1≠, 2α, 17β-trihydroxy-17α-methylandrostan-3-one to form 17β-hydroxy-17α-methyl-1-oxo-1,2,-seco-A-nor-5α-androstan-2-oic acid; and (d) reducing the 17β-hydroxy-17α-methyl-1-oxo-1,2,-seco-A-nor-5α-androstan-2-oic acid to form oxandrolone.

In another aspect of the present invention, a process is provided for the production of oxandrolone comprising the steps of: (a) oxidizing mestanolone using o-iodoxybenzoic acid (IBX) to form 17β-hydroxy-17α-methyl-5α-androst-1-en-3-one; (b) hydroxylating the 17β-hydroxy-17α-methyl-5α-androst-1-en-3-one to form 1α, 2α, 17β-trihydroxy-17α-methylandrostan-3-one; (c) cleaving the 1α, 2α, 17β-trihydroxy-17α-methylandrostan-3-one to form 17β-hydroxy-17α-methyl-1-oxo-1,2,-seco-A-nor-5α-androstan-2-oic acid; and (d) reducing the 17β-hydroxy-17α-methyl-1-oxo-1,2,-seco-A-nor-5α-androstan-2-oic acid to form oxandrolone. At least two by-products are formed in step (a) that are non-reactive to steps (b) and (c).

In a further aspect of the present invention, mestanolone is oxidized using IBX to form 17β-hydroxy-17α-methyl-5α-androst-1-en-3-one. The 17-hydroxy-17α-methyl-5α-androst-1-en-3-one is hydroxylated using osmium tetroxide to form 1α, 2α, 17β-trihydroxy-17α-methylandrostan-3-one. The 1α, 2α, 17β-trihydroxy-17α-methylandrostan-3-one is cleaved using sodium metaperiodate to form 17β-hydroxy-17α-methyl-1-oxo-1,2,-seco-A-nor-5α-androstan-2-oic acid. The 17β-hydroxy-17α-methyl-1-oxo-1,2,-seco-A-nor-5α-androstan-2-oic acid is then reduced using sodium borohydride followed by an acid treatment to form oxandrolone.

In yet another aspect of the present invention, mestanolone is reacted with IBX to form 17β-hydroxy-17α-methyl-5α-androst-1-en-3-one. The 17β-hydroxy-17α-methyl-5α-androst-1-en-3-one is reacted with osmium tetroxide and N-methylmorpholine N-oxide to form 1α, 2α, 17β-trihydroxy-17α-methylandrostan-3-one. The 1α, 2α, 17β-trihydroxy-17α-methylandrostan-3-one is reacted with sodium metaperiodate to form 17β-hydroxy-17α-methyl-1-oxo-1,2,-seco-A-nor-5α-androstan-2-oic acid. Oxandrolone is then formed from the 17β-hydroxy-17α-methyl-1-oxo-1,2,-seco-A-nor-5α-androstan-2-oic acid by reacting the 17β-hydroxy-17α-methyl-1-oxo-1,2,-seco-A-nor-5α-androstan-2-oic acid with sodium borohydride followed by an acid treatment comprising addition of hydrochloric acid.

BRIEF DESCRIPTION OF THE DRAWING

The FIGURE illustrates the general synthetic scheme of the present invention.

DETAILED DESCRIPTION OF THE INVENTION

According to the present invention, oxandrolone is produced using mestanolone (i.e., 17β-hydroxy-17α-methyl-5α-androstan-3-one) as a starting material. The mestanolone is oxidized in order to form an enone intermediate (i.e., 17β-hydroxy-17α-methyl-5α-androst-1-en-3-one). The enone is hydroxylated to form an intermediate triol (i.e., 1α, 2α, 17β-trihydroxy-17α-methylandrostan-3-one), which is cleaved to form an intermediate acid (i.e., 17β-hydroxy-17α-methyl-1-oxo-1,2,-seco-A-nor-5α-androstan-2-oic acid). The acid is reduced to form oxandrolone.

The mestanolone is preferably oxidized using IBX (o-iodoxybenzoic acid), and the enone is preferably hydroxylated using osmium tetroxide. In one preferred aspect, a catalytic amount of osmium tetroxide is used along with N-methylmorpholine N-oxide. The triol is preferably cleaved using sodium metaperiodate, and the acid is preferably reduced using sodium borohydride followed by an acid treatment (i.e., addition of an acid or acids). In one preferred embodiment, the acid treatment comprises addition of hydrochloric acid.

Unless otherwise stated, the following terms used in the specification and claims have the meanings given below:

"Oxidize" or "oxidizing" means to undergo or cause to undergo a chemical reaction resulting in a loss of electrons or hydrogen, or a gain of oxygen.

"Hydroxylate" or "hydroxylating" means to undergo or cause to undergo a chemical reaction resulting in an addition of one or more hydroxyl groups.

"Cleave" or "cleaving" means to undergo or cause to undergo a chemical reaction resulting in loss of a covalent bond between two atoms.

"Reduce" or "reducing" means to undergo or cause to undergo a chemical reaction resulting in a gain of electrons or hydrogen, or a loss of oxygen.

The present invention provides a method for forming oxandrolone in high overall yields (e.g., 30–40%) and high purity (e.g., greater than 98%). This method provides advantages over other known methods for producing oxandrolone as well as other methods of performing the synthesis steps disclosed herein. For example, by using IBX as the oxidizing agent in the first step, the enone intermediate is produced in the present invention in high yields (e.g., about 70%). Although the use of IBX results in the production of one or more by-products (typically at least two by-products), the by-products are non-reactive to the subsequent hydroxylation and cleavage steps of the process, resulting in quantitative yields of the desired products. The nonreactive by-products do not affect the recovery of oxandrolone as (1) the oxandrolone may be easily removed or separated (e.g., by crystallization of the final product) after the reduction step of the process or (2) the by-products may be easily removed or separated after the reduction step of the process. Thus, the present invention advantageously provides an efficient process for the production of oxandrolone that results in decreased production time, decreased production cost, and increased overall yield as compared to known methods. The present invention enables the production of oxandrolone without the need for chromatography, such as silica gel column chromatography, at any step of the process. Thus, the desired product may be obtained through the steps of the present invention in sufficiently pure form as to substantially eliminate purification procedures normally required, e.g., chromatography. A preferred embodiment of the process of the present invention also avoids the use of (or is performed in the substantial absence of) lead tetraacetate, a highly toxic compound used in known methods for oxidative cleavage.

The general synthetic scheme of the present invention is shown in the FIGURE. The steps of the general method are: step (a), oxidation of mestanolone to form an enone; step (b), hydroxylation of the enone to form a triol; step (c), cleavage of the triol to form an acid; and step (d), reduction of the acid to form oxandrolone.

Step (a) is as follows:

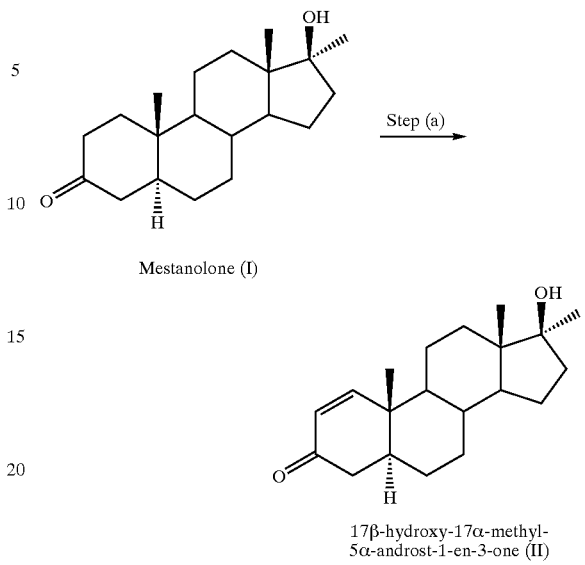

In this step, mestanolone (I) is reacted with an oxidizing agent or agents in a suitable solvent or solvent mixture at elevated temperature to produce the enone (II) (i.e., 17β-hydroxy-17α-methyl-5α-androst-1-en-3-one). The oxidizing agent is preferably IBX, although other oxidizing agents such as, for example, bis(acetoxy)iodobenzene, and iodosobenzene may also be used. The molar ratio of mestanolone to oxidizing agent is typically from about 1:1 to about 1:2, preferably about 1:1.5. When IBX is used as the oxidizing agent, the molar ratio of mestanolone to IBX is preferably about 1:1.5. Suitable solvents or solvent mixtures include fluorobenzene or toluene with dimethyl sulfoxide (DMSO). Preferably, the solvent mixture will be toluene and DMSO. The volume ratio of toluene to DMSO typically will be about 1:1 to about 3:1, preferably about 2:1. The reaction is performed at an elevated temperature, typically in a temperature range from about 55° C. to about 85° C., preferably in a temperature range from about 60° C. to about 75° C., and more preferably in a temperature range from about 65° C. to about 70° C. The reactants generally are heated for about 6 to about 48 hours. The product yield of this reaction and the purity of the reaction product will depend upon the oxidizing agent and the reaction temperature. When IBX is used as the oxidizing agent, the yield is typically about 65% to about 75% in a temperature range of about 68° C. to about 72° C. As mentioned above, when IBX is used as the oxidizing agent, two by-products are typically produced, but, advantageously, are nonreactive to the subsequent hydroxylation and cleavage steps (i.e., steps (b) and (c)).

IBX (o-iodoxybenzoic acid) is a cheap, nontoxic reagent. It may be produced from any known method. Preferably, the IBX will be prepared as illustrated in the synthesis scheme shown below:

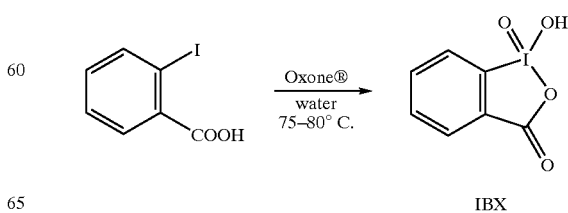

According to the reaction scheme, 2-iodobenzoic acid is reacted with Oxone® brand monopersulfate compound (available from DuPont®) in water at about 75° C. to about 80° C. to form IBX.

Step (b) is as follows:

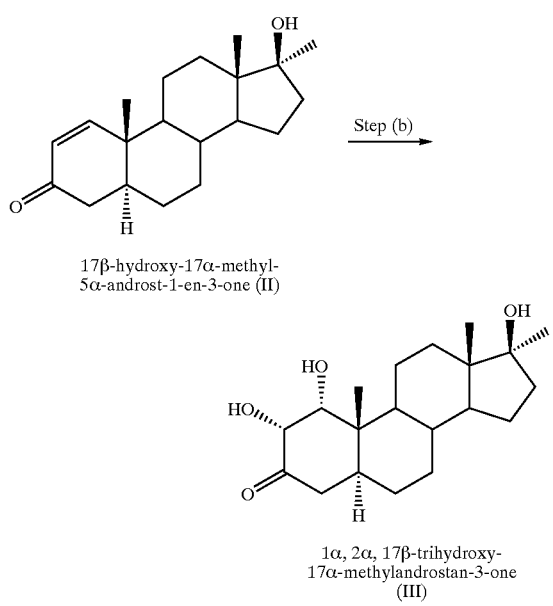

17β-hydroxy-17α-methyl-
5α-androst-1-en-3-one (II)

1α, 2α, 17β-trihydroxy-
17α-methylandrostan-3-one
(III)

In step (b), the enone (II) produced in step (a) (i.e., 17β-hydroxy-17α-methyl-5α-androst-1-en-3-one) is reacted with a stereospecific hydroxylating agent or agents in a suitable solvent or solvent mixture to produce the intermediate triol (III) (i.e., 1α, 2α, 17β-trihydroxy-17α-methylandrostan-3-one). The hydroxylating agent is preferably osmium tetroxide, although other hydroxylating agents such as, for example, potassium permanganate, may be used. In one preferred embodiment, osmium tetroxide is used in a catalytic amount along with N-methylmorpholine N-oxide (e.g., a 50% aqueous solution thereof). Osmium tetroxide may also be used alone or in a catalytic amount in combination with t-butyl hydroperoxide, barium chlorate, or another suitable oxidant or oxidants. The molar ratio of enone to hydroxylating agent is typically from about 1:0.001 to about 1:0.01, preferably about 1:0.005. Suitable solvents or solvent mixtures include tetrahydrofuran, dioxane, acetone, t-butyl alcohol, water, and mixtures thereof. Preferably, the solvent mixture will be tetrahydrofuran (THF) and acetone. The volume ratio of THF to acetone typically will be about 1:3 to about 3:1, preferably about 1:1. The reaction generally is performed at room temperature, typically in a temperature range from about 10° C. to about 50° C., preferably in a temperature range from about 20° C. to about 30° C. The reactants are typically allowed to react for about 6 to about 24 hours. The product yield of this reaction and the purity of the reaction product will depend upon the hydroxylating agent and the reaction temperature. When osmium tetroxide is used in a catalytic amount along with N-methylmorpholine N-oxide as a cooxidant, the yield is typically about 75% to about 95% in a temperature range of about 20° C. to about 30° C.

Step (c) is as follows:

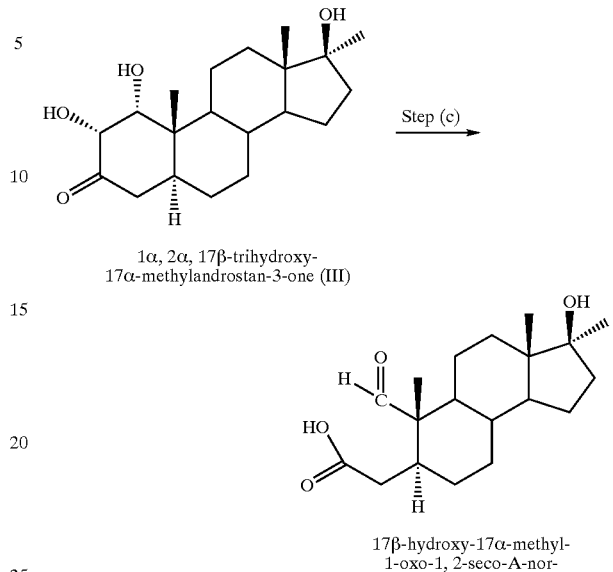

1α, 2α, 17β-trihydroxy-
17α-methylandrostan-3-one (III)

17β-hydroxy-17α-methyl-
1-oxo-1, 2-seco-A-nor-
5α-androstan-2-oic acid (IV)

In this step, the triol (III) produced in step (b) (i.e., 1α, 2α,17β-trihydroxy-17α-methylandrostan-3-one) is reacted with an oxidative cleaving agent or agents in a suitable solvent or solvent mixture to produce the intermediate acid (IV) (i.e., 17β-hydroxy-17α-methyl-1-oxo-1,2,-seco-A-nor-5α-androstan-2-oic acid). The cleaving agent is typically sodium metaperiodate, although other cleaving agents may be used such as, for example, lead tetraacetate and ozone. The molar ratio of triol to cleaving agent is typically about 1:3 to about 1:1, preferably about 1:2. Suitable solvents or solvent mixtures include tetrahydrofuran, dichloromethane, dioxane, water, tert-butyl alcohol, and mixtures thereof. Preferably, the solvent mixture will be THF and dichloromethane. The volume ratio of THF to dichloromethane typically will be about 1:1 to about 1:5, preferably about 1:4. The reaction is performed at room temperature, typically in a temperature range from about 20° C. to about 40° C., preferably in a temperature range from about 25° C. to about 35° C. The reactants are typically allowed to react for about 6 to about 24 hours. The product yield of this reaction and the purity of the reaction product will depend upon the cleaving agent and the reaction temperature. When sodium metaperiodate is used as the cleaving agent, the yield is typically about 75% to about 95% in a temperature range of about 25° C. to about 30° C.

Step (d) is as follows:

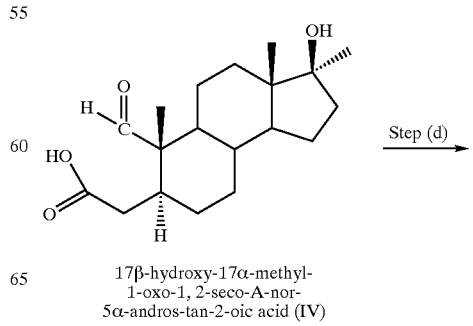

17β-hydroxy-17α-methyl-
1-oxo-1, 2-seco-A-nor-
5α-andros-tan-2-oic acid (IV)

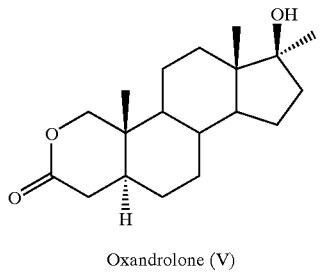

Oxandrolone (V)

In this step, the acid (IV) produced in step (c) (i.e., 17β-hydroxy-17α-methyl-1-oxo-1,2,-seco-A-nor-5α-androstan-2-oic acid) is reacted with a reducing agent or agents in a suitable solvent or solvent mixture followed by an acid treatment (i.e., the addition of an acid or acids) to produce oxandrolone (V). The reducing agent is typically sodium borohydride, although other reducing agents such as, for example, lithium tri-tert-butoxyaluminum hydride, may also be used. The molar ratio of intermediate acid (IV) to reducing agent is typically about 1:1 to about 1:2, preferably about 1:1.5. When sodium borohydride is used as the reducing agent, the molar ratio of the intermediate acid (IV) to sodium borohydride is preferably about 1:1.5. The acid treatment comprises addition of a suitable acid or acids such as, for example, an organic and/or an inorganic acid, and preferably comprises addition of a mineral acid such as, for example, hydrochloric acid. In one embodiment, sodium borohydride is used as the reducing agent and hydrochloric acid is added as the acid treatment. The solution is typically acidified by the acid treatment to a pH range from about 1 to about 4, preferably from about 2 to about 3. Suitable solvents or solvent mixtures include tetrahydrofuran, dimethylformamide, dioxane, and mixtures thereof. Preferably, the solvent is dimethylformamide. The reaction is performed at low temperature, typically in a temperature range from about 0° C. to about 25° C., preferably in a temperature range from about 10° C. to about 20° C. The reactants are typically allowed to react for about 6 to about 24 hours. The product yield of this reaction and the purity of the reaction product will depend upon the reducing agent and the reaction temperature. When sodium borohydride is used as the reducing agent followed by an acid treatment comprising addition of hydrochloric acid, the temperature range will be about 0° C. to about 20° C. The overall yield for the entire process is typically about 30% to about 40%.

As discussed above, when IBX is used as the oxidizing agent in step (a) of the process, two by-products are typically produced. These two by-products do not react in steps (b) and (c), but are believed to react in step (d), although the by-products do not affect the isolation of the final product. The final product may be isolated from the by-products by techniques such as crystallization of the oxandrolone, which typically results in a product that is greater than 98% pure.

Alternatively, the by-products may be separated by techniques such as crystallization. In addition, isolation of the final product does not require time-consuming procedures such as chromatography.

EXAMPLES

The invention will be further explained by the following illustrative examples that are intended to be non-limiting.

Example 1

Synthesis of 17α-methyl-17α-hydroxy-5α-androst-1-en-3-one

A mixture of mestanolone (55.3 g, 0.182 mol) and IBX (76.5 g, 0.273 mol, 1.5eq.) in 1800 ml toluene:DMSO (2:1) was heated at 65–70° C. for 48 h after which time the beginning clear solution turned into a suspension. TLC (thin layer chromatography) indicated the disappearance of starting mestanolone and the appearance of the desired product and two by-products. After cooling to RT (room temperature), the reaction mixture was filtered on a frit and solid washed with ethyl acetate (2×200 ml). The filtrate was diluted with 1000 ml of ethyl acetate and the resulting organic phase was washed with 1000 ml each of 5% $NaHCO_3$, water, and brine. After drying over sodium sulfate, removal of the solvents on a rotavapor gave ~56.0 g of a crude products mixture containing the required product (i.e., 17α-methyl-17β-hydroxy-5α-androst-1-en-3-one) along with two minor by-products.

Example 2

Synthesis of 1 α, 2α, 17β-trihydroxy-17α-methylandrostan-3-one

The crude product mixture obtained in Example 1 above (56.0 g, 20 mmol) was dissolved in 600 ml THF and then diluted with 600 ml of acetone. To this solution was added a 50 wt % aqueous solution of N-methylmorpholine N-oxide (65.4 g, 280 mmol) followed by a 1% aqueous solution of $OsO_4$ (24 ml, 0.94 mmol) and 28 ml of water. The reaction mixture was stirred at RT overnight (~18 hr). TLC showed the complete disappearance of the enone and the appearance of a polar product; the by-products from Example 1 remained unaffected. 2.0 g of potassium carbonate was added to the mixture and stirred for 30 minutes, and the volatiles were removed on a rotavapor at RT. The reaction mixture was taken up in 2000 ml each of ethyl acetate and water and was then shaken vigorously in a sep-funnel. After removing the aqueous phase, the organic phase was washed with 1000 ml each of water, 5% aqueous solution of sodium metabisulphite, water, and brine. Afer drying over sodium sulfate, removal of solvents on rotavapor yielded 61.6 g of a crude products mixture.

Example 3

Synthesis of 17β-hydroxy-17α-methyl-1-oxo-1, 2-seco-A-nor-5α-androstan-2-oic Acid The crude product mixture obtained from Example 2 above (61.6 g, 185.0 mmol) was dissolved in 350 ml THF and then the resulting solution was diluted with 1400 ml of dichloromethane. Powdered sodium metaperiodate (87.5 g, 409.0 mmol, 2.2 eq.) was added in one lot to the stirring mixture followed by 50 ml of water. The resulting mixture was vigorously stirred for 24 hr after which time all of the starting material disappeared as indicated by TLC. Anhydrous sodium sulfate was added to the reaction mixture and allowed to stir for 10 minutes. The solids were filtered off on a frit and washed with dichloromethane (2×360 ml). Removal of the solvents from the filtrate yielded 60.2 g of white solid.

Example 4

Synthesis of 17β-hydroxy-17α-methyl-2-oxa-5α-androstan-3-one

The white product obtained in Example 3 above (60.2 g, 186.6 mmol) was dissolved in 250.0 mL DMF (dimethyl formamide). The DMF (250.0 mL) solution of crude acid (60.2 g, 186.6 mmol) was added drop wise to a stirring suspension of sodium borohydride (10.7 g, 189.4 mmol, 1.5 eq.) in 160.0 ml of DMF at 0–5° C. The reaction mixture was stirred for 24 hr at RT and then cooled back to 0–5° C. 1 N NaOH (103.0 ml) aqueous solution was then added drop wise to the stirring solution while maintaining the temperature below 10° C. The reaction mixture was diluted with 740.0 ml of water, transferred to a sep-funnel, and extracted with 2×600 ml of dichloromethane followed by 300 ml of ether. The aqueous layer was transferred back to a flask containing a stirrer. 1200 ml of a 1:1 mixture of THF and ethyl acetate was added to the aqueous layer and then acidified by drop wise addition of a 3N aqueous hydrochloric acid solution (~160 ml was needed to get pH of 2–3) while keeping the temperature around 10° C. The resulting mixture was poured into a sep-funnel containing 600 ml of ethyl acetate. The organic phase was separated and then successively washed with water (2×500 ml) and brine. After drying over sodium sulfate, the solution was partially concentrated on a rotavapor yielding white crystalline solid, which was collected on a frit and washed with ether to give 18.6 g (33% overall yield) of oxandrolone.

While the invention has been described in detail and with reference to specific embodiments thereof, it will be apparent to one skilled in the art that various changes and modifications can be made without departing from the spirit and scope of the invention.

What is claimed is:

1. A process for the production of 17β-hydroxy-17α-methyl-5α-androst-1-en-3-one, the process comprising reacting mestanolone with IBX to form 17β-hydroxy-17α-methyl-5α-androst-1-en-3-one.

2. The process of claim 1 wherein mestanolone and IBX are present in a molar ratio from about 1:1 to about 1:2.

3. The process of claim 1 wherein the reaction is performed in a temperature range from about 55° C. to about 85° C.

4. The process of claim 1 wherein the reaction is performed from about 6 hours to about 48 hours.

5. The process of claim 1 wherein at least two by-products are formed.

6. The process of claim 1 wherein 17β-hydroxy-17α-methyl-5α-androst-1-en-3-one is formed at a yield of about 65% to about 75%.

7. The process of claim 1 wherein:
   mestanolone and IBX are present in a molar ratio from about 1:1 to about 1:2;
   the reaction is performed in a temperature range from about 55° C. to about 85° C. for about 6 hours to about 48 hours; and
   17β-hydroxy-17α-methyl-5α-androst-1-en-3-one is formed at a yield of about 65% to about 75%.

8. The process of claim 7 wherein at least two by-products are formed.

9. The process of claim 1 wherein:
   mestanolone and IBX are present in a molar ratio of about 1:1.5;
   the reaction is performed in a temperature range from about 60° C. to about 75° C. for about 6 hours to about 48 hours;
   17β-hydroxy-17α-methyl-5α-androst-1-en-3-one is formed at a yield of about 65% to about 75%; and
   at least two by-products are formed.

10. The process of claim 9 wherein the reaction is performed in a temperature range from about 65° C. to about 70° C.

11. The process of claim 10 wherein the reaction is performed in a mixture of toluene and dimethyl sulfoxide.

* * * * *